US00PP33071P2

(12) United States Plant Patent
Dirr

(10) Patent No.: US PP33,071 P2
(45) Date of Patent: May 18, 2021

(54) ***ABELIA* PLANT NAMED 'BAILBELIAONE'**

(50) Latin Name: ***Abelia* x *grandiflora***
Varietal Denomination: Bailbeliaone

(71) Applicant: Bailey Nurseries Inc., Newport, MN (US)

(72) Inventor: Michael A. Dirr, Bogart, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 16/998,964

(22) Filed: Aug. 20, 2020

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Penny J. Aguirre

(57) ABSTRACT

A new cultivar of *Abelia* x *grandiflora* plant named 'Bailbeliaone', that is characterized by its compact, mounded, low growing plant habit, its flowers that are white in color with light pink colored sepals, its strong young stems that are red-bronze in color when young, its variegated foliage with green centers and pink margins when young and green centers with white margins when mature, its ease of growth in a container, and its vigorous root system.

2 Drawing Sheets

Botanical classification: *Abelia* x *grandiflora*.
Varietal denomination: 'Bailbeliaone'.

BACKGROUND OF THE INVENTION

The present invention relates to a new and distinct cultivar of *Abelia* x *grandiflora* and will be referred to hereafter by its cultivar name, 'Bailbeliaone'. 'Bailbeliaone' represents a new *Abelia*, a semi-evergreen shrub grown for landscape use.

The new cultivar was discovered by one of the Inventors in summer of 2007 as a naturally occurring branch mutation of *Abelia* x *grandiflora* 'Mardi Gras' (U.S. Pat. No. 15,203) growing in a cultivated garden in Athens, Ga.

Asexual reproduction of the new cultivar was first accomplished by stem cuttings by one of the Inventors in Watkinsville, Ga. in 2013. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailbeliaone' as a unique cultivar of *Abelia*.

1. 'Bailbeliaone' exhibits a compact, mounded, low growing plant habit.
2. 'Bailbeliaone' exhibits flowers that are white in color with light pink colored sepals.
3. 'Bailbeliaone' exhibits strong stems that are red-bronze in color when young.
4. 'Bailbeliaone' exhibits variegated foliage with green centers and pink margins when young and green centers with white margins when mature.
5. 'Bailbeliaone' exhibits ease of growth in a container.
6. 'Bailbeliaone' exhibits a vigorous root system.

'Mardi Gras', the parent plant of 'Bailbeliaone', is similar to 'Bailbeliaone' in having variegated foliage. 'Mardi Gras' differs from 'Bailbeliaone' in having a larger, more open and, upright plant habit, in having foliage with green centers and dark pink margins when young and creamy yellow-white margins when mature, in having leaves that are smaller in size, and in having flowers that are pink in color with dark red sepals. 'Bailbeliaone' can be most closely compared to the *Abelia* x *grandiflora* cultivar 'Conti' (U.S. Plant Pat. No. 8,472). 'Conti' differs from 'Bailbeliaone' in having unstable variegated foliage (shoots with non-variegated green leaves are common) and new growth that has margins that are purple in color and mature to white-green.

BRIEF DESCRIPTION OF THE DRAWINGS

The accompanying colored photographs illustrate the overall appearance and distinct characteristics of the new *Abelia*. The photographs were taken of a two year-old plant as grown outdoors in a 11.8-liter container in Watkinsville, Ga.

The photograph in FIG. 1 provides a top view of a plant of 'Bailbeliaone' in summer.

Figure 1:
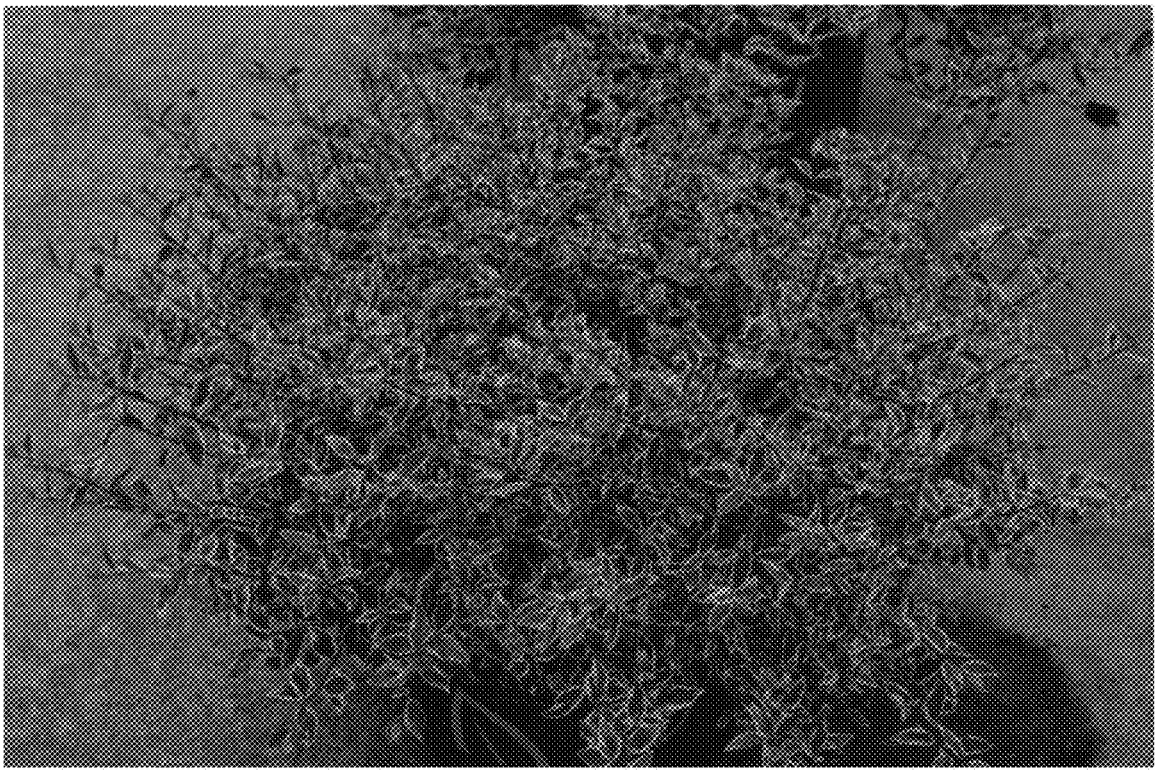
Figure 2:
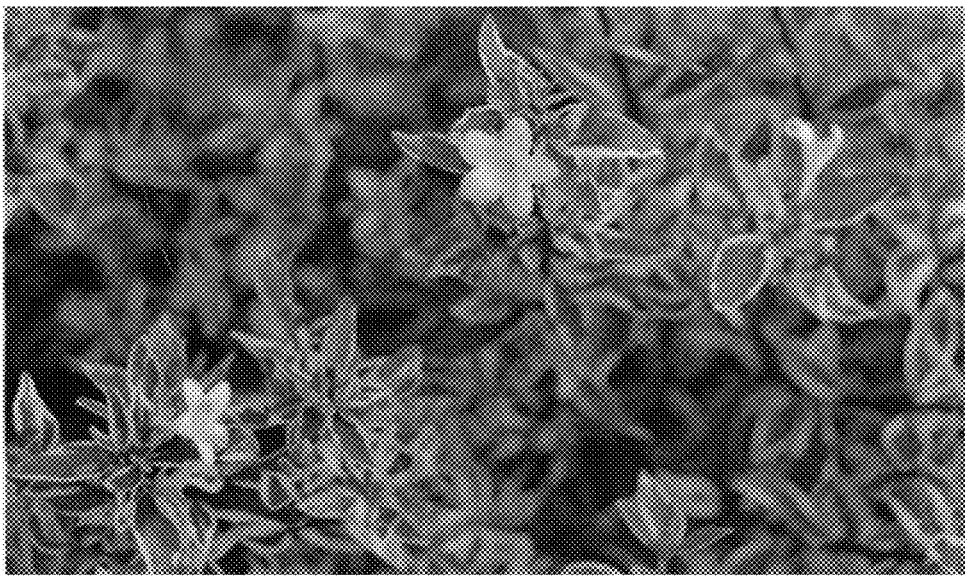

The photograph in FIG. 2 provides a close-up view of flowers and the new growth of 'Bailbeliaone'.

Figure 3:
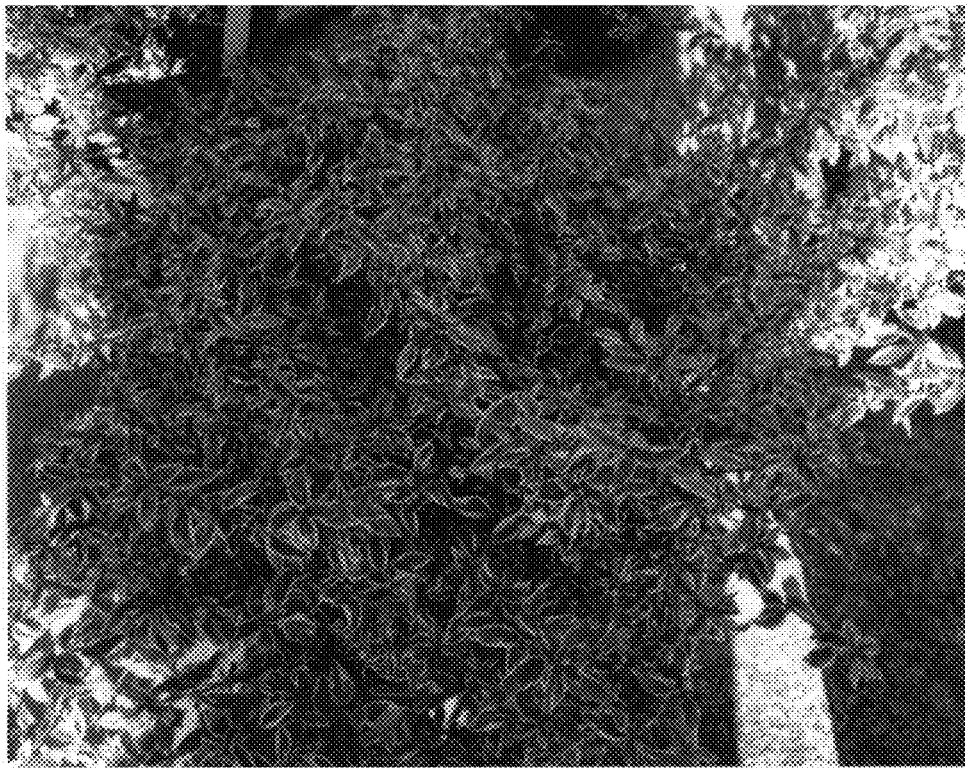

The photograph in FIG. 3 provides a close-up view of the fall foliage of 'Bailbeliaone'.

The colors in the photographs are as close as possible with the photographic and printing technology utilized and the color values cited in the Detailed Botanical Description accurately describe the colors of the new *Abelia*.

DETAILED BOTANICAL DESCRIPTION

The following is a detailed description of two-year-old plant as grown outdoors in an 11.8-Liter container in Watkinsville, Ga. The phenotype of the new cultivar may vary with variations in environmental, climatic, and cultural conditions, as it has not been tested under all possible environmental conditions. The color determination is in accordance with The 2007 Colour Chart of The Royal Horticultural Society, London, England, except where general color terms of ordinary dictionary significance are used.

General description:

*Blooming period.*—May to June and then sporadically until frost in Watkinsville, Ga.

*Plant type.*—Semi-evergreen flowering shrub.

*Plant habit.*—Compact, mounded to spreading, well branched.

*Height and spread.*—An average of 46 cm in height and 61 cm in spread as a two-year-old plant in a container.

*Cold hardiness.*—At least in U.S.D.A. Zones 6 to 9.

*Diseases and pests.*—No resistance to diseases or pests has been observed.

*Root description.*—Fine and fibrous, prolific and well branched.

*Propagation.*—Terminal stem cuttings.

*Root development.*—Roots initiate in an average of 21 days in the summer at 32° C.

*Growth rate.*—Vigorous.

Stem description:

*Stem color.*—Young (first year); 46A, mature wood and bark; 200A (199D under exfoliating bark).

*Stem size.*—An average of 39 cm in length and 2.5 mm in diameter, 1 cm in diameter on first year growth and 3 cm in diameter on second year and older stems, trunk; 1 cm in diameter at the soil line.

*Stem quantity.*—An average of 14 main branches from the trunk, average of 16 lateral branches per main stem.

*Stem shape.*—Round.

*Stem surface.*—Finely pubescent on young stems, exfoliating bark on second year and after.

*Stem strength.*—Young; flexible, mature; easily broken.

*Internode.*—An average of 1 cm in length.

*Branching habit.*—Freely branching, pruning enhances lateral branching.

Foliage description:

*Leaf division.*—Simple.

*Leaf attachment.*—Petiolate.

*Leaf arrangement.*—Opposite.

*Leaf number.*—An average of 86 per stem 25 cm in length.

*Leaf shape.*—Ovate-elliptic.

*Leaf size.*—An average of 2 cm in length and 1 cm in width.

*Leaf apex.*—Acute.

*Leaf base.*—Rounded to cuneate.

*Leaf surface.*—Upper surface; shiny and finely pubescent, lower surface; dull and finely pubescent.

*Leaf venation.*—Pinnate, color; young and mature leaves upper and lower surfaces; 1A.

*Leaf margin.*—Entire to serrate.

*Leaf color.*—Young upper surface; 137B with irregular margins 157D and N155D, flushed with 39A and 38D, young lower surface; 137C with irregular margins N155D, flushed with 39B and 38D, mature upper surface; 137A with irregular margins 155A, and mature lower surface; 137B with irregular margins 155A.

*Petioles.*—An average of 1 mm in diameter and 2 mm in length, both surfaces finely pubescent, color; upper surface mature foliage, 39A and lower surface mature leaves 137B.

*Leaf buds.*—Opposite in arrangement, conical in shape, comprised of 2 pairs of bud scales, finely pubescent surface, an average of 2 mm in length and 1 mm in width, 46A in color.

Flower description:

*Inflorescence type.*—Terminal and axillary panicles of campanulate flowers.

*Inflorescence aspect.*—Upwards and outwards.

*Inflorescence size.*—An average of 4 cm in height and 3 cm in width.

*Inflorescence density of flowers.*—Moderate.

*Flower fragrance.*—Faint, pleasant.

*Flower quantity.*—An average of 15 per inflorescence.

*Flower lastingness.*—An average of 7 days, self-cleaning, persistent showy sepals last for about 5 months.

*Flower buds.*—Obelliptic in shape, an average of 4 mm in diameter and 2.2 cm in length, 36C in color.

*Flower aspect.*—All directions.

*Flower shape.*—Campanulate with base fused.

*Flower size.*—About 2 cm in depth and 1 cm in diameter.

*Petals.*—An average of 5, spatulate in shape, an average of 5 mm in length and 4 mm in width, entire margin, obtuse apex, fused base, upper and lower surface; smooth and sparsely pubescent, color upper and lower surfaces 155D.

*Calyx.*—Rotate, an average of 4 mm in length and 2 mm in diameter, fused at the base, 38A in color, glabrous surface.

*Sepals.*—4 to 5, an average of 2 mm in width and 6 mm in length, elliptical in shape, entire margin, acute apex, fused base, smooth upper and lower surface, color; upper and lower surfaces 141C with the tip 39B.

*Peduncles.*—An average of 1 cm in length and 2 mm in diameter, strong, color: 200A, finely pubescent surface.

*Pedicels.*—An average of 3 mm in length and 0.5 mm in width, strong, color; 178B, finely pubescent surface.

Reproductive organs:

*Gynoecium.*—1 pistil, an average of 2 cm in length, glabrous surface, stigma; round in shape, an average of 1 mm in diameter, 155D in color, style; an average of 1.7 cm in length and 1 mm in width, 155D in color, ovary; inferior, an average of 7 mm in length and 1 mm in width, 173B in color.

*Androcoecium.*—About 5 stamens, an average of 5 mm in length, anthers; an average of 2 mm in length and 1 mm in width, 155D in color, filaments; an average of 4 mm in length and 0.5 mm in width, 155D in color, pollen is low in quantity and 155D in color.

*Fruit and seed.*—One-seeded, tubular achene, coriaceous surface, an average of 7 mm in length and 2 mm in width, mature color; 177A.

It is claimed:

1. A new and distinct cultivar of *Abelia* plant named 'Bailbeliaone' as herein illustrated and described.

* * * * *